(12) United States Patent
Jean et al.

(10) Patent No.: US 6,601,956 B1
(45) Date of Patent: Aug. 5, 2003

(54) METHOD AND APPARATUS FOR THE SIMULTANEOUS DETERMINATION OF SURFACE TOPOMETRY AND BIOMETRY OF THE EYE

(76) Inventors: Benedikt Jean, Auf der Schcibe 30, D-88138 Sigmarszell (DE); Thomas K. Bende, Jahnstrasse 16, D-72116 Mossingen (DE); Adolf F. Fercher, Hassreitersteig 3/11, A-1230 Vienna (AT)

( * ) Notice: Subject to any disclaimer, the term of this patent is extended or adjusted under 35 U.S.C. 154(b) by 0 days.

(21) Appl. No.: 09/831,793
(22) PCT Filed: Nov. 15, 1999
(86) PCT No.: PCT/EP99/08782
§ 371 (c)(1), (2), (4) Date: Jul. 30, 2001
(87) PCT Pub. No.: WO00/28884
PCT Pub. Date: May 25, 2000

(30) Foreign Application Priority Data

Nov. 13, 1998 (DE) .......................................... 198 52 331
Jun. 9, 1999 (DE) .......................................... 199 26 274

(51) Int. Cl.[7] ................................................ A61B 3/10
(52) U.S. Cl. ..................................................... 351/212
(58) Field of Search ................................. 351/205, 206, 351/209, 210, 211, 212, 213–216, 221, 246; 356/450

(56) References Cited

U.S. PATENT DOCUMENTS

| | | | |
|---|---|---|---|
| 5,491,524 A | * | 2/1996 | Hellmuth et al. ........... 351/212 |
| 5,493,109 A | | 2/1996 | Wei et al. |
| 5,526,073 A | | 6/1996 | Mattioli |
| 5,684,562 A | * | 11/1997 | Fujieda ....................... 351/212 |

FOREIGN PATENT DOCUMENTS

| | | |
|---|---|---|
| DE | 4322620 | 7/1993 |
| DE | 4325494 | 7/1993 |
| DE | 19713623 | 4/1997 |
| EP | 0697611 | 2/1996 |
| EP | 0705562 | 4/1996 |
| WO | WO97/42891 | 11/1997 |

* cited by examiner

Primary Examiner—Marvin M. Lateef
Assistant Examiner—John R. Sanders
(74) Attorney, Agent, or Firm—Steven J. Hultquist; Marianne Fuierer; Yongzhi Yang

(57) ABSTRACT

An apparatus (10') for detecting the surface topography of a cornea (24) of an eye (22) by dynamic or static projection of a pattern onto the surface of the cornea and detection of the pattern reflected by the cornea, providing preferably simultaneous detection of at least one optical property of a layer disposed beneath the cornea.

23 Claims, 4 Drawing Sheets

METHOD AND APPARATUS FOR THE SIMULTANEOUS DETERMINATION OF SURFACE TOPOMETRY AND BIOMETRY OF THE EYE

The invention relates to a method and an apparatus for detecting the surface topometry of the cornea of the eye with means for a dynamic or static projection of a pattern onto the surface of the cornea and means for detecting the pattern reflected or mirrored by the cornea. The term "layer" shall be understood hereinunder within the terms of tomography and is not limited to thin border layers between zones of different refractive indexes.

A wide variety of methods and apparatuses for detecting the surface topography of the cornea are known in which patterns are projected statically (e.g. DE 43 25 494 A1 or U.S. Pat. No. 5,684,562) or dynamically (e.g. DE 43 22 620 A1) onto the cornea and the pattern reflected or mirrored from the cornea is detected. Such methods are usually called video-keratometry or as ring projection according to Placido and have proven their worth in general practice. They allow a point-by-point measurement of the corneal surface (mostly with more than eight thousand measuring points) within a few milliseconds.

The topography of the surface of the cornea is deduced from the position of the projection points and the relative relationship of these points that usually form a ring pattern. The reflected pattern is usually recorded by a CCD array, with the CCD array, e.g. the CCD array of a video camera, usually being disposed coaxially and concentrically at the end of a so-called Placido's cone. This set-up leads to the consequence, however, that central corneal region which has a diameter of approx. 0.5 mm cannot be detected during the measurement, although it is the central optical zone of the cornea in particular that relevantly determines the refractive power of the eye and typically forms the pass-through point of the visual axis. The so-called Stiles-Crawford effect leads to the consequence that the central corneal zone which is free from any patterns during the projection of Placido's patterns plays a special role with respect to the peripheral corneal regions in the eye's projection system.

Moreover, video-keratometry, which occasionally is also designated as video-topography, is unable to supply any information on the back surface of the cornea and the lower sections of the refractive system of the eye, in particular the front side and back side of the lens. The geometry of the boundary surface, the depth of the anterior chamber of the eye, the boundary surface properties and the topography of the lens, the distribution of density and the scattering body arrangements in the lens and the depth of the posterior chamber of the eye (as defined by the distance between lens and retina) are the prerequisites for increasing the precision of refractive measures on the cornea and for implantation-surgical interventions on the lens for the computer-aided detection and analysis of the refractive system of the optical properties of the entired eye in a patient.

However, some of these devices (DE 43 25 494 A1 or U.S. Pat. No. 5,684,562) provide means to alien the projected pattern to the eye or vice versa.

These alignment means may provide certain information about the eye beneath the cornea by processing some light being reflected by inner structures of the eye. Such information is fairly vague especially along the optical axis of the eye.

As an alternative, the U.S. Pat. No. 5,491,524 suggests to use optical coherence tomography (OCT) to provide for topographic results. However, this method is not able to provide information about the geometrical position at which the measurement takes place. Especially, a natural movement of the eye cannot be compensated.

Keeping this in mind, the invention is based on the object of providing a method and an apparatus which allow detecting in a simple and rapid manner both the entire substantial surface topography of the cornea and also at least one optical property of the layers of the eye disposed under the cornea with comparely high accuracy.

This object is achieved by an apparatus of the kind mentioned above in which means are provided for detecting at least one optical property of a layer disposed beneath the cornea of the eye comprising coherence tomographic means. This object is also achieved by a method of the kind mentioned above in which at least one optical property of a layer of the eye disposed beneath the cornea is detected parallel to the detecting process of the surface tomography of the cornea, via coherence tomography.

Such an set-up and such a method enable the required measurements to be performed in one process. This is substantially more pleasant for the person undergoing such a measurement. Moreover, this set-up also ensures that a detection of the optical properties of layers beneath the cornea occurs with a required local calibration because such a local calibration is enabled by the detection of the surface topography of the cornea. It is thus no longer necessary that the person rigidly stares into the focusing light during the measurement of the optical properties of layers disposed beneath the cornea, which is physiological not possible. Rather, smaller deviations can be measured accordingly by the detected surface topography. Thus, the apparatus and the method in accordance with the invention allow determining the optical properties of the entire eye with adequately high local precision for the first time.

For example, the apparatus in accordance with the invention may comprise at least one laser light source, a detector for detecting laser beams generated by the laser light source and means for splitting the beams and deflecting at least a part of the beams into the eye and deflecting onto the detector parts of the laser beams reflected in the eye.

Such an apparatus allows comparing the surface topography and the overall refraction of the eye and thus determining the influence and the data of the optical media disposed deeper in the eye. In addition, scattering image analyses can be obtained from the organ parts of the eye. Particularly the topographically non-detectable central portion can be detected topometrically and topographically with the apparatus.

Accordingly, laser beams can be produced in a method in accordance with the invention by means of at least one laser light source and can be split and deflected in such a way that at least a part of the beams is guided into the eye, with parts of the laser beams reflected by the eye being guided to the detector and being detected by the detector.

Depending on the respective problem to be solved, the method can he performed in such a way that the profile of the wave front of laser beams directed at the eye are compared with the profile of the wave front reflected by the eye. As an alternative or in addition, the method can also be performed in such a way that the running periods of laser beams emitted into the eye are determined.

The measurements will be particularly precise and easy to perform when a Placido Topometer is used for projecting the pattern onto the surface of the cornea. In this process, the laser beam can be guided on their path towards the eye and back through the beam of the Placido Topometer for detecting the optical properties of layers disposed beneath the cornea. For this purpose suitable deflection means such as tilted mirrors or deviating prisms are used.

For determining the optical properties of layers disposed beneath the cornea by it is possible to introduce a known beam profile or a known wave front of a laser source in the zone of the pupillary opening and to direct the same onto the cornea and the lower sections of the eye. By determining the profile form of a wave front reflected by the eye and a comparison with the wave front sent into the eye it is possible to detect the optical properties. A Hartmann-Shack detector is particularly suitable for this purpose. Such an arrangement will yield a particularly precise picture of the optical properties of the layers of the eye which are disposed beneath the cornea.

Alternatively or cumulatively, it is also possible to provide optical coherence tomography (OCT) in order to determine the optical properties of the layers disposed beneath the cornea. Such a coherence tomography has proven its worth and reliably supplies tomographs from the entire eye and also contains information on the layer thickness of the individual portions of the eye which are relevant for the refraction (biometry). In particular, the method and apparatus in accordance with the invention can be used for a substantial improvement of optical coherence tomography because movement artefacts can be respectively corrected by the continuous simultaneous detection of the surface topography of the cornea. Mathematical calculations based on these surface topographies can be used to compensate for corneal movements during data acquisition and can thus also be used to compensate the movements errors for the OCT measurement.

The corneal topography in the central corneal area can also be determined in particular in such a way that in the central Placido-ring-free area of the cornea a short-coherent measurement system, in particular a laser measurement system, is mirrored in and is aimed at the cornea and the lower sections of the eye coaxially to an optical axis extending through the pupil and the retina. In addition, the OCT offers the advantage to measure the morphology and other optical features of the different layers inside the eye. For example, these data can be used to measure and analyze the corneal wound healing process in the stromal tissue after refractive surgery.

As the time needed to capture the OCT information is substantially longer than the topography acquisition time, several—instead of only one—topographies should be made during the said OCT-acquisition in order to detect and compensate movement artifacts, due to accidental eye movements.

The yet unsolved problem of the alignment of the measuring device with the cornea can be solved as follows: OCT is well as the wavefront sensing device can be correlated to the topographer's reference point (e.g. the patients line of sight). This is achieved by using the same fixation light for the topography and the wavefront sensing or OCT, enabling to calculate in x/y coordinates the starting point of the data analisis.

OCT also provides morphological information of the relevant optical components of the eye (cornea, lens, vitreous) by acquiring layer-specific information, obtained by appropriate adjustment of the z-axis. In this manner morphological, optical, densitometric data from inside the cornea and the lens can be obtained. As a diagnostic and topometric tool for refractive surgery, only the OCT can provide such data, relevant for diagnosis and therapy. The said morphological information can also be obtained by wavelength selection based on OCT alone or in combination with z-axis variation based data acquisition.

OCT measurements of more than one point (centrally and paracentrally) allow the measurement of the lens in situ. Such measurements can be achieved by splitting the OCT (either statically using prisms, or dynamically using a scanning device) and subsequent assessment of differences ot each beams run-time Beam splitting in one of the described manners allows triangulation measurements of the lens position, an essential morphometric information.

Apart a static projection of the placido ring pattern onto the cornea (tear film), the corneal surface topography as well as the information of the OCT scan can be obtained, using a dynamic projection of one or more light sources. In this manner, the Purcyne images (1=surface cornea, 2=retrocorneal surface, 3=anterior lens surface, 4=posterior lens surface, 5=retina) can be used to measure the said optical relevant surfaces:

Further objects and advantages of the invention are provided by the following description in conjunction with the drawings of two embodiments of the invention which are selected merely as examples and are not to be understood in any way as limiting, wherein.

Figure 3:
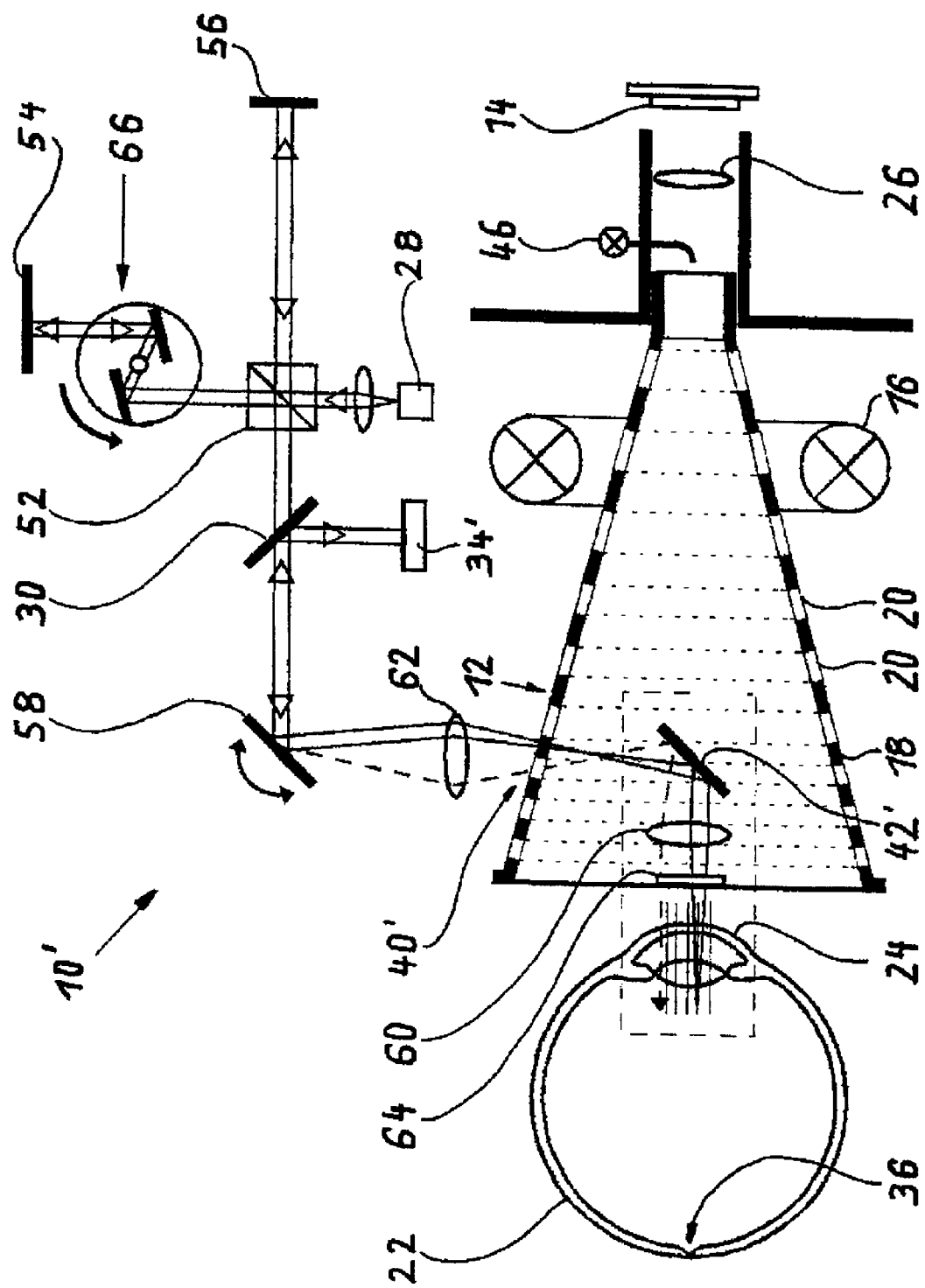
Figure 4:
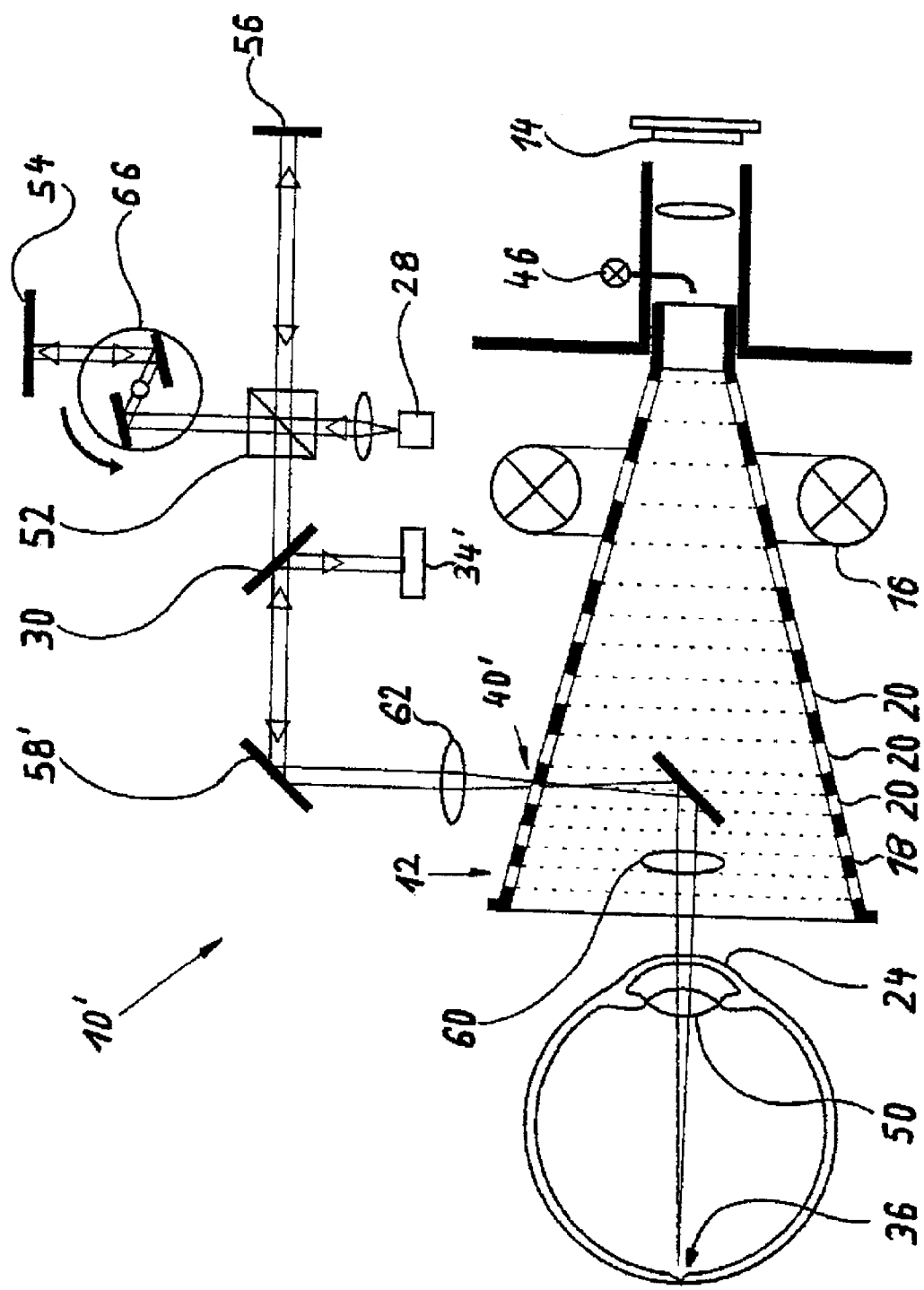

FIG. 3 schematically shows the arrangement of an apparatus with a Placido Topometer and optical coherence tomograph, with the optical coherence tomograph being set up for acquiring tomographies from the anterior section of the eye and FIG. 4 shows the apparatus pursuant to FIG. 3, but with the coherence tomograph being set up to perform scans in the middle and posterior section of the eye.

Figure 1:
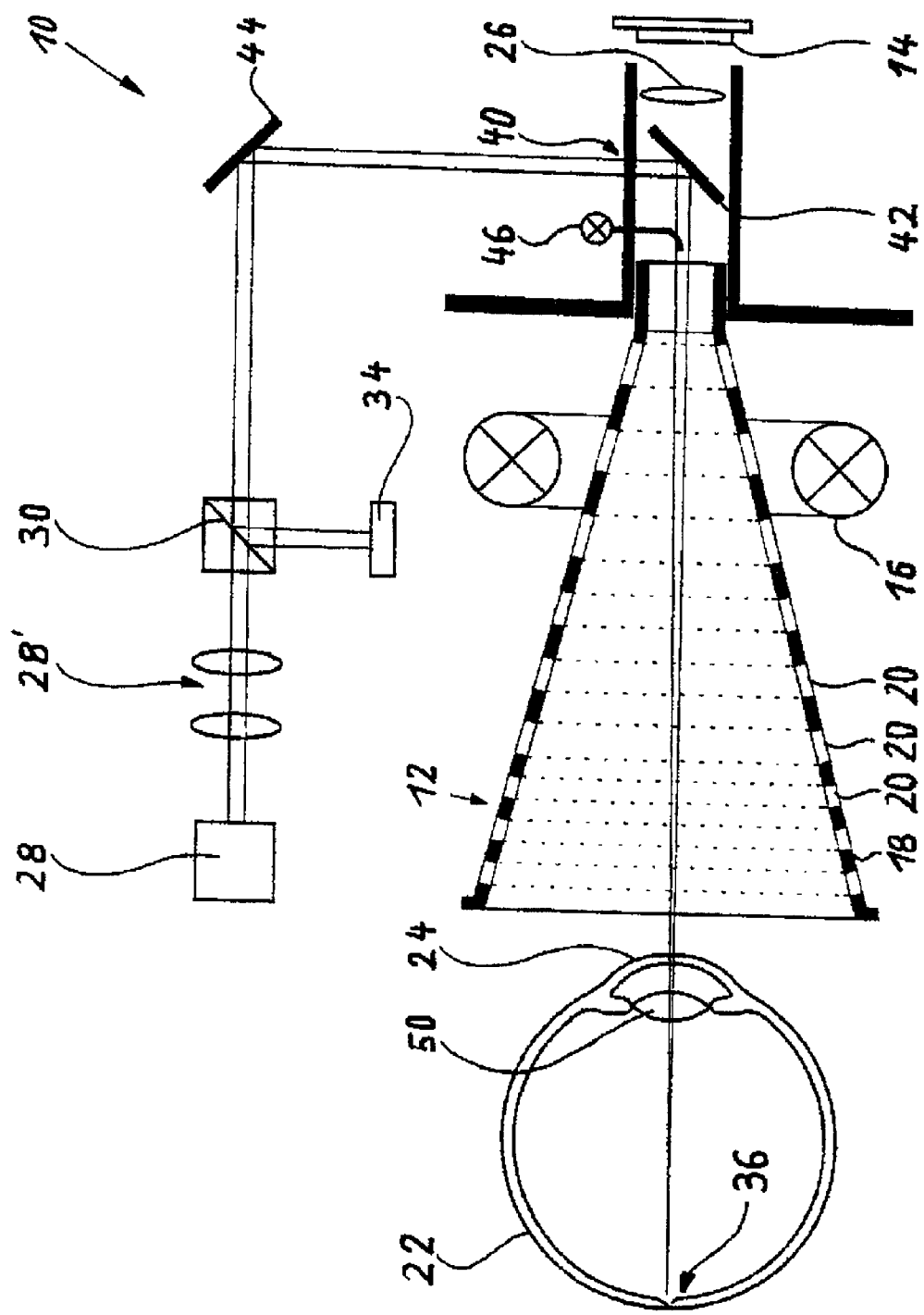
FIG. 1 shows the principal arrangement of an apparatus with a Placido Topometer and a wave front analyser.

The apparatus which is shown in FIGS. 1, 3 and 4 and is shown in its entirety with reference numerals 10 and 10' principally consists of two components, namely a Placido Topometer with a cone 12 with a random aperture angle, a CCD array 14 and an annular lamp 16 for illuminating the outside wall of the cone 18 as well as a wave front analyser (FIG. 1) or an optical coherence tomograph (FIGS. 3 and 4). A number of annularly extending apertures 20 are introduced into the outside wall of cone 18 of the Placido cone 12 of which only a limited number were provided with reference numerals for reasons of clarity of the illustration and through which the light produced by the cone lamp 16 can pass, so that a pattern is projected in the known manner on an eye 22, or more specifically a cornea 24, to be examined. The annularly extending apertures 20 can concern slots in the simplest of cases, so that the projected rings are monochromatic. It is also possible to introduce various nets or grids into the apertures so that the projected rings are pattern-coded and a simpler allocation of the rings to their gcometric origin is enabled. It is also possible to introduce different colour filters into the individual apertures in order to thus encode the projected rings in colour.

During the operation of the apparatus the luminous cone is reflected on a reflecting surface such as the surface of the cornea 24. The reflected image is reproduced via a lens 26 on the CCD array 14 of a video camera. The image of the surface with the reflected image of the cone rings is then supplied to an evaluator unit, e.g. a PC or a workstation, for further processing.

The Placido Topometer, which in the illustrated examples is a Placido ring topometer, allows measurement the surface the cornea 24 within a few milliseconds by recording usually more than 8,000 measuring points. This has the disadvantage, however, that it does not supply any information from deeper sections of the eye. This information, however, can be supplied by the wave front analysis (FIGS. 1 and 2) or the coherence tomography (FIGS. 3 and 4), for the purpose of which the Placido Topometer is provided in accordance with the invention with a beam profile or wave front analyser (FIGS. 1 and 2) or an optical coherence tomograph (FIGS. 3 and 4).

The beam profile or wave front analyser consists of a laser source 28 which emits a beam profile in the known form, e.g. a Gaussian beam profile. This laser source can emit an infrared or other light of known optical path length. The wave front 32 is react out via a beam splitter 30 by means of a respective detector field, e.g. by means of a Hartmann-Shack sensor 34. The profile of the wave front 32 is determined from the acquired data. The portion of the laser beam that is not mirrored out is beamed into the eye 22. The diameter of the laser beam depends on the pupil's diameter and can optionally be widened or reduced by a lens system (telescope 28') depending on the type of the laser source. The wave front which is reflected on the retina 36 or the rear pole of the eye 22 is deflected on the partially transparent mirror (beam splitter 30) to the detector 34. The difference between the two wave fronts, namely input wave 32 and the wave 38 reflected in the eye, which were illustrated beneath one another in the right-hand upper portion of FIG. 2 next to the detector 34 to illustrate their different forms, allows drawing conclusions of the local differences in running time. This allows determining local differences in refraction. In conjunction with the surface topography it is not only possible to describe the surface of the cornea with respect to form and curvature in local coding, but also to determine the influence of the deep-lying refractory media on the overall refractive power.

In order to combine the two measuring methods an aperture 40 is introduced at any location in the beam path of the Placido Topometer (FIG. 1) through which the laser beam of the wave front analyser can be guided. A small deviation mirror 42 is attached in the interior of the Placido cone which will redirect the laser beam of the wave front analyser either parallel or under a known angle to the axis of eye to CCD array. Said deviation mirror 42 can be attached both centrally as well as outside of the centre of the Placido cone. Instead of the deviation mirror it is also possible to consider other beam-guiding objects (e.g. prisms). A further deviation mirror 44 is provided in the arrangement as shown in FIG. 1, which mirror can naturally also be omitted depending on the arrangement of the laser light source 28.

Moreover, if the laser light emitted by the laser source 28 can not be used as a so called fixation light for the patient, the apparatus is provided with an additional focusing light 46 which helps the patient being examined to keep the examined eye as steady as possible during the examination in that the same focuses on the focusing light 46, and with an evaluator 48 which is coupled with the detector 34. A central evaluation and control unit is provided in the form of a PC which both evaluates the data received from the CCD array 14 as well as from the detector 34 and simultaneously controls the apparatus according to the problem to be solved. The data thus gained can be used for example for determining the overall optical behaviour of the eye or important parts of the eye such as the eye lens 50 for example. From the radius of curvature of the surface of the cornea and the information on the total refraction of the eye it is possible for example to calculate with high precision the data of an artificial intraocular lens to be produced for a patient with a cataract.

In this process the described measurements can be performed both within a recording sequence or also sequentially. In addition, any desired combination of the individual measurements is possible within definable time intervals. Both measuring processes can be co-ordinated through respective automatic control processes which control both the sequence of recordings as well as the selection of the required information according to the problem to be solved. According to the problem to be solved, which is selected by the operator through a control menu for example, the measurements to be performed are chosen automatically and will then be executed in the sequence most appropriate for the respective application. The results of the measurement can be output for example on a screen or printer in the form of colour-coded cards for the radii or elevation values of artificial lenses and/or as a computer file for further use such as during the automatic production of artificial lenses.

The combination of the methods leads to a qualitatively novel and previously unachievable quantitative description of the eye in respect of diagnostics and therapeutics. In combination with the method for determining the absolute co-ordinates in free space (cf. DE 195 163 09 A1) as developed by the applicant and a rapid calculation of ray tracing, the possibility is given for the first time of determining not only the optical boundary surfaces, but also the optical quality of the media in a metrologically objective manner. With the help of a Ray Tracing program, it is possible in vivo and in situ to quantify the overall refractive system, based upon the data as acquired by the apparatus. Biometric data allow the individual analysis and prospective calculation of the visual acuity, contrast sensitivity as functional parameters. At the same time, the consequence of a planed surgical intervention (e.g. intrastromal ring, phacic IOL, PRK, LASIK) can be calculated and thus—in limits— predicted by an "expert" software program.

As a result of the combination of the two methods, automated laser surgery is provided with a previously unattainable comprehensive topometrical/topographical illustration of the cornea, ranging from the outermost peripheral cornea up to the pass-through point of the visual axis through the cornea. This on the other hand, leads to the opportunity to use the complete data record (possibly with its linkage to ray tracing programs) to introduce the individually optimal ablation pattern for the front surface of the cornea with photo-ablative lasers. The data thus gained can be used according to the method known under the name of "assisted or guided Topography", as a result of their completeness over the entire cross section of the cornea, to detach the ablation process from the surgeon's manual dexterity and to provide it as a data record for the automated ablation of tissue in the laser per se.

The topography of the cornea and the wave front analysis in the eye lead to new possibilities in the calculation of individually manufactured intraocular lenses. For the first time, they allow determining vision-optimised refractory conditions for the individual patient, both for medical care with contact lenses as well as with intraocular lenses. It is thus possible to seriously change the limits of previous medical care with contact lenses and with intraocular lens implants. Finally, this system is also based on an approach leading to cost reductions for the health system in general in which the additional corrective aids such as spectacles, which are still required in more than 70% of the cases, will become avoidable.

FIGS. 3 and 4 show an apparatus 10' substantially consisting of a Placido topometer with a Placido cone 12, a cone lamp 16 and a CCD array 14 as well as an optical coherence tomograph. An aperture 40' is introduced into the Placido cone 12 through which the laser beam of the coherence tomograph can be guide. A small deviating mirror 42 is attached in the interior of the Placido cone 12, which mirror will redirect the laser beam of the coherence tomograph either parallel or under a known angle to the axis of eye to CCD array. Said deviation mirror 42' can be attached both centrally as well as outside of the centre of the Placido cone. Instead of the deviation mirror it is also possible to consider other beam-guiding objects (e.g. prisms).

The coherence tomograph (OCT) per se substantially consists of a laser light source 28, with a so-called SLD laser diode being used as a laser light source for example, a prism splitter 52 which splits the laser beam onto two reference mirrors 54 and 56, a photodetector 34' which can detect the running time and the phase shift as well as the intensity behaviour of the incident laser light. A further deviation mirror 58 (FIG. 3) or 58' (FIG. 4) is provided in addition which, as is indicated in FIG. 3, can be arranged so as to be swivellable about two axes, so that it can act as an "x/y scanner". Moreover, focusing lens systems (lenses 60 and 62) for beam concentration are provided for the purpose of boundary surface detection and are positioned in such a way that the beam diameter is as small as possible at the pass-through point 40' of the laser beam through the Placido cone 12 and only a very small loss of information is incurred during the Placido measurement. A dual-beam reference mirror is further provided in the apparatus in accordance with FIG. 3, which mirror supplies a reference surface for the geometry of the cornea.

The focal point at which the laser beam is focused on its path into the eye after the last deviation mirror 42' defines the pleasuring point or the measuring plane of the coherence tomograph. In order to detect the individual boundary surfaces on the eye for example (anterior and posterior surface of the cornea, anterior and posterior surface of the lens, fundus of the eye), the focal point must be moved along the optical axis through the eye. An example is given in the embodiment as shown in FIGS. 3 and 4 by means of a rotating or oscillating double-mirror optical path length modulator 66 which is interposed in the beam path between prism splitter 52 and first reference mirror 54. As a result of the movement of the modulator, the focal point of the laser beam is guided from the anterior surface of the cornea to the fundus of the eye. A signal maximum occurs in detector 34' at each optical boundary surface. As a result of the angle encoding of the optical path length modulator it is possible to assign each reflection point to a linear measure. This means that one obtains distance information within the eye along the optical axis between each optical boundary surface. These data can be used for the overall biometry of the eye, for example.

If the deviation mirror 58, as is shown in FIG. 3, is swivellably held about two axes, a surface scan can be performed in any desired plane. For this purpose the optical path length modulator is brought to a standstill according to the desired target plane and the incoming laser beam is directed by means of the deviation mirror 58 to different pointed within the plane. In this way it is possible to measure with high precision the central portion of the cornea for example, which—as was already explained above—cannot be measured with the Placido Topometer as a result of its design. Moreover, by the defined advance of the measuring plane (rotation of the optical path length modulator) it is possible, to measure any desired number of closely following planes which will then in their entirety provide three-dimensional information on the measured volume and can supply additional information on structural changes in the optical system (scattering, absorption, reflection, etc.). Such a diagnostic statement was previously not possible.

The use of limited x/y positions (for example 3 or 4 Positions) provided by the mirror 58 allows the determination of the decentration or tilt of the lens if the surface topography is combined with the data of the OCT measurement.

Figure 2:
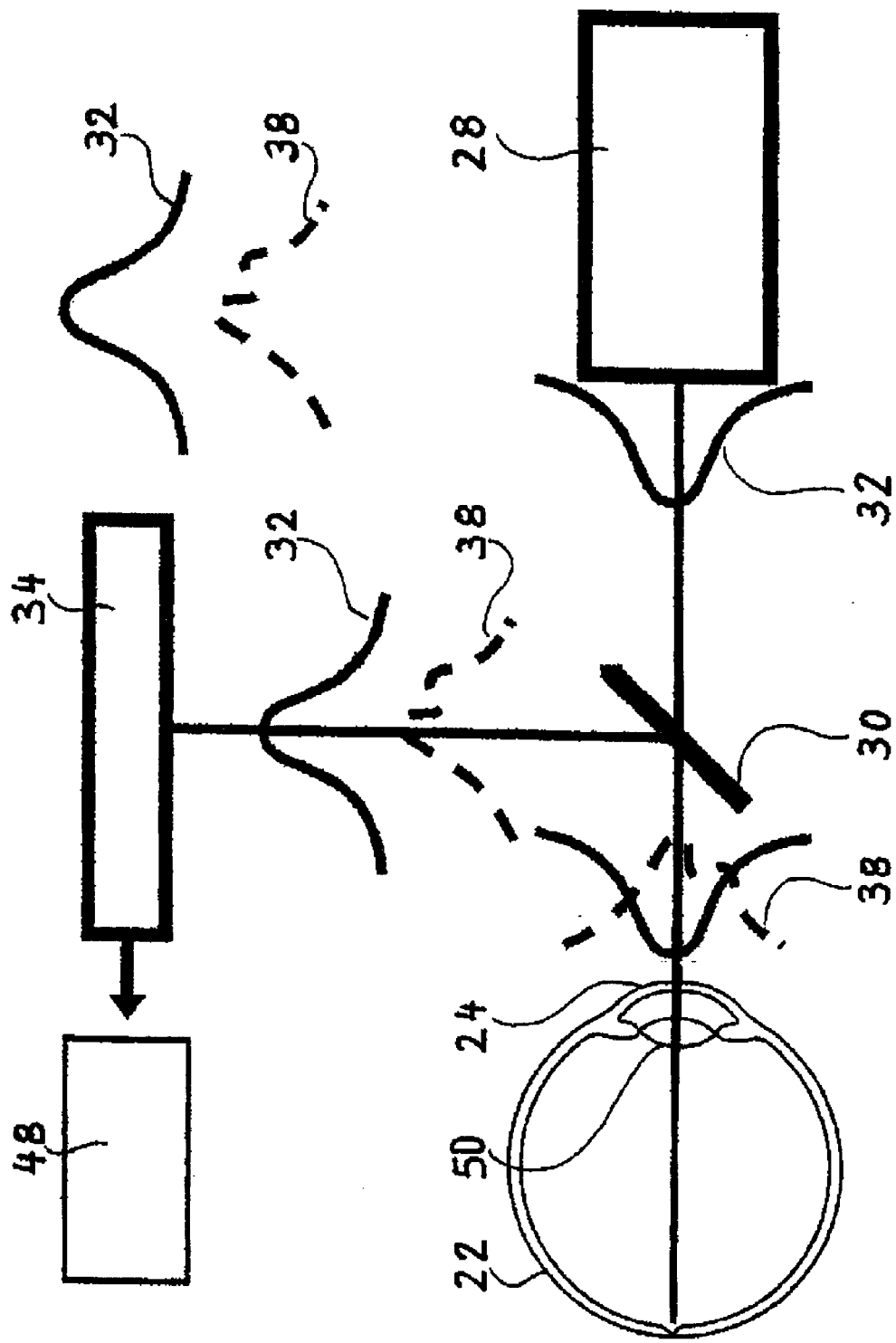
FIG. 2 shows the principal mode of operation of a wave front analyser.

As has already been mentioned in connection with the FIGS. 1 and 2, the measurements with the Placido Topometer and the coherence tomograph can be performed both simultaneously or sequentially. As has also already been explained above, the combination of Placido optometry and coherence tomography leads to a qualitatively novel and previously unachievable quantitative description of the eye in respect of diagnostics and therapeutics. With the help of the ray tracing programs it is then possible in vivo and in situ to quantify the overall refractory system after the acquisition of the data with the apparatus in accordance with the invention, including clouding of media and scar formation in the wound-healing progress. For example, apparatuses and methods in accordance with the present invention can be used to obtain layer-by-layer information on the scattering bodies, for which there is urgent need both with respect to forensic medicine as well as diagnostics. For example, after surgery on the cornea it is possible to determine an objective measure for the haze formation and wound healing without having to resort to the physically simplifying forward light scattering.

A further important application is the therapy and risk stratification of the cataract which with the increasing shift in the population's age structure will later affect up to 100% of the population. The invention allows an objective determination of the corneal clouding. Our knowledge of the other properties of the entire optical refractory system, which also includes the anterior and posterior surface of the lens and the anterior and posterior surface of the cornea as well as the depth of the anterior chamber of the eye, will allow determining therefrom the visual acuity that can objectively be expected.

An objective grading of the clouding inside the anterior chamber and the lens can be produced from the correlation between the calculated visual acuity with the clinically observed one. Even gaining objective criteria for grading the stages of clouding phenomena in vivo and in vivo alone will have far-reaching consequences for diagnosing and the therapy of highly-endemic eye diseases.

The invention also enables a qualitatively decisive improvement in the field of biometry. Conventional biometries based on ultrasonic sound which are performed prior to cataract operations and the insertion of artificial lenses operate with simplifications which in the end do not allow for an individually optimal visual result. Since the posterior surface of the cornea was not quantitatively detectable to date, it was partly not possible to determine any curvatures of the lens and possible, even minimal, decenterings and dislocations, so that the lenses to be implanted were calculated imprecisely. The socio-economic consequences of the procedure to date are considerable: up until now the theoretically possible maximum rate of visual acuity was not achieved in approx. 80% of all cases of lens implantations after cataract operations, so that cost-intensive corrections by means of spectacles were required. If tie miscalculation between RA/LA is more than three dioptres, additional problems of anisometropy can occur. The invention now allows for the first time by using surface topometry and coherence tomography and/or wave front analysis to determine a data record in a particularly simple way from which the optimal implant for every individual case can be calculated precisely.

Within the scope of the idea of the invention it is possible to provide numerous modifications and further developments are possible which relate to the type and arrangement of the Placido topometer for example. Thus it is possible for example not to produce the Placido pattern statically onto the cornea with the help of a Placido cone, but instead to produce the patterns dynamically by rotating LEDs for example. It is similarly possible that the laser light beamed in for the wave front analysis or the coherence tomography is projected statically or dynamically. The relevant aspect in the invention is in any case that topometer and wave front analyser or coherence tomograph are combined in one apparatus.

What is claimed is:

1. An apparatus for detecting the surface topography of a cornea of an eye comprising:
   (a) means for dynamic or static projection of a pattern onto the surface of the cornea;
   (b) means for detecting the pattern reflected by the cornea; and
   (c) means for detecting at least one optical property of a layer disposed beneath the cornea, wherein said means for detecting at least one optical property comprises coherence tomography means.

2. The apparatus according to claim 1, further comprising:
   (i) at least one laser light source;
   (ii) a detector for detecting laser beams generated by the laser light source; and
   (iii) means for splitting laser beams and deflecting at least a portion of the laser beams into the eye and for deflecting parts of the laser beams reflected from the eye onto the detector.

3. The apparatus according to claim 2, wherein the means for projecting the pattern onto the surface of the cornea comprises a Placido Topometer, wherein the Placido Topometer is positioned in such a way that the means for deflecting the laser beams guides the laser beams through the beam path of the Placido Topometer on their way to the eye and back again.

4. The apparatus according to claim 3, wherein the means for deflecting the laser beam is selected from the group consisting of a deviation mirror and a deviating prism which is arranged in the Placido Topometer.

5. The apparatus according to claim 2, wherein the detector for detecting the laser beams is a detector which allows the determination of the profile form of the wave front of detected laser beams.

6. The apparatus according to claim 2, wherein the detector for detecting laser beams is arranged to perform an optical coherence tomography and the means for performing an optical coherence tomography further comprises:
   (a) a prism splitter;
   (b) an optical path length modulator; and
   (c) two reference mirrors.

7. The apparatus according to claim 6, wherein the optical path length modulator is a rotating or swivelling double mirror optical path length modulator.

8. The apparatus according to claim 6, further comprising means for deflecting the laser beams guided into the eye to different points of a plane.

9. The apparatus according to claim 8, wherein the means for deflecting the laser beams guided into the eye to different points of a plane comprises at least one swivellable mirror.

10. A method for detecting the surface topography of the cornea of the eye, the method comprising:
    (a) projecting by dynamic or static projection of a pattern onto the surface of the cornea;
    (b) detecting the pattern as reflected by the cornea; and
    (c) detecting at least one optical property of a layer disposed beneath the cornea wherein said detection of said optical property of a layer disposed beneath the cornea is detected by coherence tomography.

11. The method according to claim 10, wherein the laser beams are generated by means of at least one laser light source for detecting the optical properties of the layer disposed beneath the cornea, wherein the laser beams are split and deflected in such a way that at least a part of the laser beams is guided into the eye and parts of the laser beams, that are reflected by the eye, are guided to the detector and detected by the detector.

12. The method according to claim 11, wherein the pattern being projected onto the surface of the cornea is projected by a Placido Topometer and the laser beams are guided through the beam path of the Placido Topometer on their way to the eye and back again.

13. The method according to claim 12, further comprising:
    introducing into the zone of a pupillary aperture of a eye a known beam profile and/or wave front of a laser source; and
    directing the known beam profile and/or wave front onto the cornea and the lower sections of the eye.

14. The method according to claim 13, further comprising:
    determining the profile form of the wave front of the laser beams as reflected by the eye; and
    comparing with the profile form of the wave front of the laser beams as guided into the eye.

15. The method according to claim 14, wherein determining the profile form of the wave front of the laser beams is accomplished by splitting the generated laser beams and guiding a portion directly and indirectly onto a detector while another portion is guided into the eye.

16. The method according to claim 13, wherein the overall distribution of refractive power of the eye is determined with local encoding by evaluation of the reflected wavefront.

17. The method according to claim 13, wherein information on the eye is determined from detected data and selected from the group consisting of: size and surface of a cornea, posterior surface of a cornea, optical boundary surfaces of a refractive apparatus of the eye, anterior surface of a lens, posterior surface of a lens, surface of the retina, radius of curvature, refractive power and the absolute height value of a cornea.

18. The method according to claim 17, wherein the information on the optical boundary surfaces of the refractive apparatus of the eye is determined along an optical axis from the pupillary aperture up to the retina.

19. The method according to claim 17, wherein the laser beams introduced into the eye are focused on a focal point in the eye, and the focal point is moved along the optical axis extending from the cornea to the retina and reflection maxima are determined along said optical axis.

20. The method according to claim 19, wherein the focal point is moved in a plane perpendicular to the optical axis and the reflection of the laser beams introduced into the eye is measured at different points in this plane.

21. The method according to claim 11, further comprising;

projecting Placido rings onto the eye; and directing a laser beam, with a short-coherent measuring system, in a central cornea region of the eye which is free of the Placido rings and coaxially to an optical axis and extending through the pupil and onto the retina.

22. The method according to claim 21, wherein within a magnitude of the penetration depth of the laser beams, information on optical densities and scattering values is determined by optical coherence tomography within the layer thickness of relevant components of the eye.

23. The method according to claim 22, wherein a deflection of the laser beam guided to the eye is performed by means of an x/y scanner in such a way that a quasi-three-dimensional resolution is obtained.

* * * * *